United States Patent [19]

Messina et al.

[11] 4,374,279
[45] Feb. 15, 1983

[54] PROCESS FOR THE PREPARATION OF DICUMYL PEROXIDE

[75] Inventors: Giuseppe Messina, Alghero; Mario D. Moretti, Sassari; Loreno Lorenzoni, Porto Torres, all of Italy

[73] Assignee: Euteco Impianti S.p.A., Milan, Italy

[21] Appl. No.: 325,338

[22] Filed: Nov. 27, 1981

[30] Foreign Application Priority Data

Dec. 2, 1980 [IT] Italy ................. 26346 A/80

[51] Int. Cl.$^3$ .......................................... C07C 179/06
[52] U.S. Cl. ................................................... 568/558
[58] Field of Search .......................... 568/558, 568

[56] References Cited

U.S. PATENT DOCUMENTS

| | | | |
|---|---|---|---|
| 2,691,683 | 10/1954 | Lorand et al. | 568/558 |
| 2,994,719 | 8/1961 | Farkas et al. | 568/558 |
| 3,829,503 | 8/1974 | Kato et al. | 568/558 |
| 3,954,880 | 5/1976 | Nakayama et al. | 568/558 |

FOREIGN PATENT DOCUMENTS 1243313  8/1971  United Kingdom ................ 568/558

OTHER PUBLICATIONS

Davies et al., "J. Chem. Soc.", (1966) pp. 4669-70.
Hawkins, "Organic Peroxides", (1961) E and F Spon Ltd, London pp. 26, 79, 98, 99 and 220-222.
Derwent Japanese Patent Abst., 1597064 Mitsui Pet. 6/8/64-12/18/64, vol. 3; No. 32.

*Primary Examiner*—Werren B. Lone
*Attorney, Agent, or Firm*—Brumbaugh, Graves, Donohue & Raymond

[57] ABSTRACT

A process for the preparation of dicumyl peroxide by reaction of dimethylbenzyl hydroperoxide (cumene hydroperoxide) with methyl cumyl ether is described. The reaction is carried out in the presence of a catalytic quantity of Lewis or Bronsted acids, the methanol which forms as a by-product being removed as the reaction proceeds. Furthermore, the reaction is carried out in a reaction medium consisting of the methyl cumyl ether itself, which is employed in quantities greater than the stoichiometric quantity required for the reaction with the cumene hydroperoxide.

7 Claims, No Drawings

PROCESS FOR THE PREPARATION OF DICUMYL PEROXIDE

The present invention relates to a process for the preparation of dicumyl peroxide by reaction of cumene hydroperoxide with methyl cumyl ether in the presence of a catalytic quantity of at least one Lewis, or Bronsted acid.

Dialkyl peroxides in general, and dicumyl peroxide in particular, are widely used in the art as vulcanizing agents for resins and elastomers, as cross-linking agents for polyolefins and, above all, as radical polymerization initiators for the formation of polymers and copolymers from vinyl and diene monomers. They are, for example, used in the preparation of polyvinyl chloride, polyethylene, polystyrene, polyacrynotrile, polyvinyl acetate, styrene-butadiene copolymers, alkyl-styrene resins, silicone rubber and others.

The process most generally used in the art for preparing dialkyl peroxides consists of bringing an hydroperoxide into contact with an alcohol or an olefin under reaction conditions. More particularly, dicumyl peroxide is usually prepared by the reaction of dimethyl phenyl carbinol with dimethyl benzyl hydroperoxide (cumene hydroperoxide) in the presence of an acid catalyst dissolved or dispersed in the reaction medium.

The catalyst most widely used for the preparation of dialkyl peroxides, and dicumyl peroxide in particular, are: acid earths (Y. Tsunoda et al; Kogyo Kagaku Zasshi, 63, 837-9 (1960); silica-alumina (Japanese Patent No. 15,970/64); oxalic acid (Belgian Patent No. 628,315); zinc chloride (German Patent Application No. 2,842,044); and perchloric acid (V. L. Antonosku et al. Khim Perekisnykh Soedin Akad. Nauk. USSR, Inst. Obshch. i Neorgan. Khim., 1963, 240-8 and German Patent Application No. 2,062,054).

Dicumyl peroxide may also be prepared by the reaction of alpha-methyl styrene with cumene hydroperoxide, as described in German Patent Applications Nos. 2,035,127 and 2,016,108 and in Japanese Patent Application No. 7,952,005.

The disadvantages of using dimethyl phenyl carbinol in the process for the preparation of dicumyl peroxide lie essentially in the formation of water as the by-product of the reaction, which reduces the activity of the catalyst as a result of dilution thereof and sometimes even by interaction with the catalyst itself.

Furthermore it is generally necessary to use a solvent as the reaction medium in order to avoid overhigh, and hence dangerous, concentrations of the dicumyl peroxide in the reaction medium. Since dimethyl phenyl carbinol is scarcely suited to act as the solvent, it is necessary to use other substances with resultant procedural complications and increased costs. Furthermore, dimethyl phenyl carbinol is not a product which is readily available. It is obtained by the chemical reduction of cumene hydroperoxide, the reaction optionally being carried out in the presence of reducing catalyst. The cost of the dimethyl phenyl carbinol is thus greater than that of the cumene hydroperoxide from which it is obtained. In addition, in the separation of the dimethyl phenyl carbinol by distillation, alpha-methyl styrene forms which is difficult to separate from the carbinol. The conversion of the alphamethyl styrene into dimethyl phenyl carbinol is, on the other hand, problematical due to the somewhat unfavourable equilibrium constant of the hydration reaction.

On the other hand, the use of alpha-methyl styrene in the process for the preparation of dicumyl peroxide has disadvantages due to its tendency to form dimers. Consequently the yields and the selectivity towards the useful reaction product are lower. In addition, the by-products which form are difficult to separate from the dicumyl peroxide. Finally alpha-methyl styrene is scarcely suited to act as the solvent medium for the reaction so that other substances must be used, with the complications already described.

The object of the present invention is to provide a process for the production of dicumyl peroxide which is free, or substantially free, from the disadvantages of the processes of the known art. More particularly it is found that these disadvantages may be overcome, or at least greatly reduced, by reacting methyl ether with cumene hydroperoxide in the presence of a catalytic quantity of a substance of an acidic nature and removing the methanol gradually from the reaction medium as it forms as the by-product of the reaction.

Accordingly, in the present invention, cumene hydroperoxide is brought into contact with a molar excess of methyl cumyl ether and moreover, the reaction is carried out in the presence of a catalytic quantity of at least one acid selected from the Lewis or Bronsted acids, the methanol which forms as the by-product being removed gradually from the reaction medium and the dicumyl peroxide finally being recovered from the reaction medium.

The reaction which brings about the formation of the dicumyl peroxide is as follows:

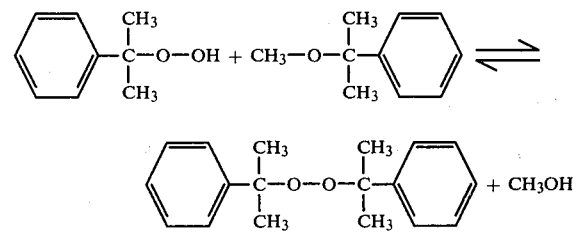

It is noted from the equation given above that methanol is formed as the by-product of the reaction, this being particularly advantageous in that methanol is volatile and hence can easily be removed from the reaction medium. Consequently the equilibrium is displaced in favour of the dicumyl peroxide and, in addition, deleterious effects resulting from excessively long contact of the methanol with the dicumyl peroxide are avoided.

The reaction described above is catalysed by Lewis acids, such as, for example, boron, aluminium, phosphorus and antimony halides and by Bronsted acids such as perchloric, para-toluene sulphonic, hydrochloric and hydrobromic acids. It is particularly advantageous to use boron halides either as such, or in the form of complexes such as, for example, boron trifluoride diethyl etherate.

The quantity of catalyst used depends on the nature of the catalyst itself and generally varies within the range of from 0.05 to 5% by weight with respect to the weight of the cumene hydroperoxide. Preferred catalytic quantities are within the range of 0.1 to 2% by weight of the weight of the hydroperoxide.

According to the present invention a molar excess of methyl cumyl ether over the cumene hydroperoxide is used, the molar ratio between the methyl cumyl ether and the cumene hydroperoxide generally being within a range of values of from 1.3/1 to 10/1 and preferably from 2/1 to 4/1.

The reaction which brings about the formation of the dicumyl peroxide occurs, in general, at a temperature of from ambient (20° to 25° C.) to 100° C., with preferred temperatures within the range 30° to 60° C.

The removal of the methanol from the reaction mixture is assisted by keeping the pressure below atmospheric, for example a pressure of 100 to 300 mm of mercury and/or by using a flow of inert gas such as nitrogen.

At the end of the reaction, the reaction mixture is neutralised, for example by treatment with an aqueous base or by passage over basic exchange resins. The methyl cumyl ether is then separated by vaporisation and the dicumyl peroxide is crystallised from the concentrated solution obtained. Alternatively, the dicumyl peroxide is separated from the neutralised reaction mixture by distillation under high vacuum or by steam distillation.

The process of the present invention has a great many advantages. Indeed, methyl cumyl ether is less expensive than dimethyl phenyl carbinol and may easily be prepared from methanol and alpha-methyl styrene under the action of acidic catalysts. Pure alpha-methyl styrene may be used for the purpose, or the flow of alpha-methyl styrene (resulting from the production of phenol from cumene *via* cumene hydroperoxide) which contains impurities such as acetophenone, butyl benzene, cumene and others may be used. The said flow, containing alpha-methyl styrene, is reacted with methanol to produce methyl cumyl ether and the reaction product obtained is used directly in the process of the present invention to prepare dicumyl peroxide. The possibility of using this methyl cumyl ether is a substantial advantage.

It is also possible and advantageous to use technical cumene hydroperoxide resulting from the production of phenol from cumene in the process of the present invention. The said technical cumene hydroperoxide contains a quantity of cumene hydroperoxide of the order of 85 to 90% by weight, the remaining percentage consisting essentially of dimethyl phenyl carbinol, acetophenone, cumene and butyl benzene.

In the present invention, the methyl cumyl ether also acts as a solvent and the methanol which forms is removed relatively easily.

It should also be noted that the yields, rate and selectivity of the reaction are greater when methyl cumyl ether is used than in processes in which dimethyl phenyl carbonol or alpha-methyl styrene is used.

Finally, the use of the ether allows smaller quantities of catalyst to be used, thus rendering the subsequent treatments of neutralising and washing the reaction product easier and more economical.

EXAMPLE 1

There are loaded into a 100 ml glass flask, 30 grams of methyl cumyl ether (0.2 moles), 0.1 ml of boron trifluoride diethyl etherate and 9 grams of technical cumen hydroperoxide (0.05 moles) containing 88% by weight of cumene hydroperoxide, 7% by weight of dimethyl phenyl carbinol, 1.2% by weight of acetophenone, 3.5% by weight of cumene and 0.3% by weight of butyl benzene.

The mixture is heated to 45° C. in a thermostatically controlled bath, with stirring and a pressure of 200 mmHg is applied. After two hours, a 97% molar conversion of the cumene hydroperoxide is achieved with a yield of 94% of dicumyl peroxide.

In addition to the dicumyl peroxide and the unreacted methyl cumyl ether, the reaction mixture contains dimethyl phenyl carbinol, acetophenone and cumene resulting from the flow of the technical cumene hydroperoxide introduced and, furthermore, small quantities of phenol (0.7%) and acetone resulting from the acidic hydrolysis of the cumene hydroperoxide and small quantities of alpha-methyl styrene resulting from the decomposition of the methyl cumyl ether.

This reaction mixture is first neutralised by treatment with an aqueous base, the unreacted methyl cumyl ether is then distilled off and finally the dicumyl peroxide is separated by crystallisation.

EXAMPLE 2

There are loaded into a 100 ml glass flask, 30 grams of methyl cumyl ether (0.2 moles), 0.1 ml of boron trifluoride diethyl etherate and 9 grams of technical cumene hydroperoxide (0.05 moles) having the same composition as that used in Example 1. The mixture is heated to 60° C. with stirring and maintained at a pressure of 200 mmHg. After 30 minutes the conversion of the cumene hydroperoxide is 100% with a yield of 99.8% of dicumyl peroxide.

The reaction mixture contains only traces of alphamethyl styrene as a by-product.

The dicumyl peroxide is separated from the reaction mixture in the manner described in Example 1.

EXAMPLE 3

There are loaded into a 100 ml glass flask, 30 grams of methyl cumyl ether (0.2 moles), 0.3 ml of phosphorus oxychloride ($POCl_3$) and 9 grams of technical cumene hydroperoxide with a composition identical to that of Example 1.

The mixture is heated to 45° C. with stirring and at a pressure of 200 mmHg.

After two hours 98.6% of the cumene hydroperoxide is converted, with a yield of dicumyl peroxide of 81.1%.

The reaction mixture contains small quantities of phenol and acetone resulting from the hydrolysis of the cumene hydroperoxide and of alpha-methyl styrene resulting from the decomposition of the methyl cumyl ether, as well as the dimethyl phenyl carbinol, acetophenone and cumene present in the technical cumene hydroperoxide used.

The dicumyl peroxide is separated from the reaction mixture in the manner explained in Example 1.

EXAMPLE 4

A flow resulting from the process for the preparation of phenol from cumene, *via* cumene hydroperoxide, containing alpha-methyl styrene, cumene and butyl benzenes is reacted with excess methanol in the presence of an acid catalyst.

After neutralisation of the catalyst and removal of the unreacted methanol by distillation, a mixture is obtained having the following composition: 50% by weight of methyl cumyl ether, 35% by weight of cumene, 10% by weight of alpha-methyl styrene, and 5% by weight of butyl benzenes.

60 grams of this mixture are loaded into a 100 ml flask and 0.17 ml of boron trifluoride diethyl etherate and 9 grams of technical cumene hydroperoxide with a composition identical to that of Example 1, are added.

The mixture is heated to 45° C. with stirring and at a pressure of 200 mmHg.

After 90 minutes the cumene hydroperoxide is completely converted with a selectivity towards the dicumyl peroxide of 87%.

The reaction mixture contains small quantities of phenol and acetone (resulting from the hydrolysis of the cumene hydroperoxide) as well as dimers of alphamethyl styrene as by-products.

The dicumyl peroxide is separated from the reaction mixture as in Example 1.

We claim:

1. A process for the preparation of dicumyl peroxide which comprises:
(a) reacting cumene hydroperoxide with a molar excess of methyl cumyl ether in the presence of from 0.05% to 5% by wt. with respect to the weight of cumene hydroperoxide of a catalyst consisting of boron trifluoride or boron trifluoride etherates,
(b) maintaining the temperature in the reaction medium from about 100° C., and
(c) removing the methanol which forms during the reaction from the reaction mixture, while the reaction proceeds.

2. A process according to claim 1 wherein the said catalyst is boron trifluoride diethyl etherate.

3. A process according to claim 1 wherein the said molar excess of methyl cumyl ether is from 1.3/1 to 10/1.

4. A process according to claim 1 wherein the said methanol is removed at a reduced pressure of from about 100 mm Hg (136 millibar) to about 300 mm Hg (408 millibar).

5. A process according to claim 1 which comprises neutralising the reaction mixture, after the cumene hydroperoxide is substantially reacted, and then distilling off the unreacted methyl cumyl ether and finally recovering the dicymyl peroxide by crystallization.

6. A process according to claim 1 to 5 wherein the said cumene hydroperoxide is of technical grade with a cumene hydroperoxide content higher than about 85% by weight.

7. A process according to claim 6 wherein the said methyl cumyl ether is prepared by reaction of alphamethyl styrene (resulting from the production of phenol via cumene hydroperoxide) with methanol in presence of acidic catalysts and used directly as such.

* * * * *

UNITED STATES PATENT AND TRADEMARK OFFICE
CERTIFICATE OF CORRECTION

PATENT NO. : 4,374,279
DATED : February 15, 1983
INVENTOR(S) : Giuseppe Messina et al.

It is certified that error appears in the above-identified patent and that said Letters Patent is hereby corrected as shown below:

On the Title Page in the section entitled FOREIGN PATENT DOCUMENTS, insert --628315  5/1963  Belgium...568/558 --.

Signed and Sealed this

Twenty-seventh Day of September 1983

[SEAL]

Attest:

GERALD J. MOSSINGHOFF

Attesting Officer

Commissioner of Patents and Trademarks